United States Patent [19]

Remmereit

[11] Patent Number: 6,034,132
[45] Date of Patent: Mar. 7, 2000

[54] METHOD OF REDUCING BODYWEIGHT AND TREATING OBESITY

[75] Inventor: Jan Remmereit, Volda, Norway

[73] Assignee: Natural Nutrition Ltd. AS, Norway

[21] Appl. No.: 09/044,289

[22] Filed: Mar. 19, 1998

[30] Foreign Application Priority Data

Jan. 5, 1998 [JP] Japan .................................. 10-000550

[51] Int. Cl.$^7$ .................................................. A61K 31/20
[52] U.S. Cl. ........................................................... 514/560
[58] Field of Search ............................................. 514/560

[56] References Cited

U.S. PATENT DOCUMENTS

| | | | |
|---|---|---|---|
| 4,393,049 | 7/1983 | Horrobin ................................. | 424/145 |
| 5,017,614 | 5/1991 | Pariza et al. ............................ | 514/558 |
| 5,070,104 | 12/1991 | Pariza et al. ............................ | 514/549 |
| 5,208,356 | 5/1993 | Pariza et al. ............................ | 554/79 |
| 5,428,072 | 6/1995 | Cook et al. ............................. | 514/560 |
| 5,430,066 | 7/1995 | Cook et al. ............................. | 514/558 |
| 5,554,646 | 9/1996 | Cook et al. ............................. | 514/560 |
| 5,585,400 | 12/1996 | Cook et al. ............................. | 514/560 |
| 5,674,901 | 10/1997 | Cook et al. ............................. | 514/558 |
| 5,725,873 | 3/1998 | Cook et al. ............................. | 424/442 |

FOREIGN PATENT DOCUMENTS

| | | |
|---|---|---|
| 0 779 033 A1 | 6/1997 | European Pat. Off. . |
| WO96/34855 | 11/1996 | WIPO . |
| WO97/37546 | 10/1997 | WIPO . |
| WO97/46118 | 12/1997 | WIPO . |
| WO97/46230 | 12/1997 | WIPO . |
| WO98/05318 | 2/1998 | WIPO . |
| WO98/05319 | 2/1998 | WIPO . |

OTHER PUBLICATIONS

Pariza, M., Chemistry & Industry (12), 464–466, Jun. 16, 1997.

Pariza, M., Food Labelling News, 3(36), 20–21, Jun. 8, 1995.

Stedman's Medical Dictionary (Houghton Mifflin Co.), 1995.

Primary Examiner—Phyllis G. Spivack
Attorney, Agent, or Firm—Medlen & Carroll, LLP

[57] ABSTRACT

The present invention discloses method for reducing body weight and treating obesity. The method comprises administering a nutritionally effective amount of conjugated linoleic acid to a human. The conjugated linoleic acid may be provided in the form of a free fatty acid in a pill, or as a component of a prepared food product.

8 Claims, No Drawings

METHOD OF REDUCING BODYWEIGHT AND TREATING OBESITY

FIELD OF THE INVENTION

This invention relates to the administration of a dietary supplement, conjugated linoleic acid, to induce bodyweight reduction, thereby providing a treatment for obesity.

BACKGROUND

Obesity is the most common disorder of the developed world. The ready availability of food in most areas, a shift to relatively sedentary lifestyles, and changing food sources have contributed to this problem.

Researchers have hypothesized that recent changes in food sources have led to an imbalance in the optimal ratio of fatty acid intake. These imbalances may influence obesity. Specifically, modern diets have increased amounts of omega-6 fatty acids as compared to omega-3 fatty acids, as noted in Simopoulos, "Evolutionary Aspects of Diet: Fatty Acids, Insulin Resistance and Obesity", in *Obesity: New Directions in Assessment and Management*, VanItallie and Simonpoulos ed., The Charles Press, Philadelphia, 241–61 (1995). Omega-6 fatty acids are represented by linoleic acid and omega-3 fatty acids are represented by alpha-linolenic acid. A balance between omega-6 and omega-3 fatty acids existed for most of human history and has now been changed to a ratio of about 20 to 25:1 in the favor of omega-6 fatty acids. This increase in omega-6 fatty acids is due the increased intake of vegetable oils and increased amounts saturated and monounsaturated fatty acids (depot fat) in domestic meat as compared to meat from wild game. The replacement of saturated fats with unsaturated fats has been widely recommended, resulting in increased intake of omega-6 fatty acids from vegetable oils and trans fatty acids from margarine. This means that humans have been exposed to pharmacological doses of omega-6 fatty acids from the first time in their evolutionary history.

Trans fatty acids are rarely found in nature and are produced by the hydrogenation of vegetable oils. Studies indicate that uncommon isomers of polyunsaturated fatty acids and trans fatty acids interfere with normal omega-3 and omega-6 fatty acid metabolism, inducing significant partial deficiencies of omega-3 and omega-6 essential fatty acids, as suggested by Holman et al., Proc. Nat. Acad. Sci. USA 88:4830–34 (1991). Further evidence of disturbed omega-6 metabolism associated with obesity has been obtained from the Zucker rat model, and correlated to humans and multiloci obese mouse models. Feeding studies showed that animals gavaged with gamma linoleic acid (18:3w6) exhibited reduced food intake and reduced weight gain with return of liver arachidonic acid levels to normal. (Sere VanItallie, supra, p. 82 et seq.). Since linoleic acid is an essential precursor in the biosynthesis of arachidonic acid, the correlation of an increase in the latter by gavage of the former is a predictable outcome. However, a careful analysis of the metabolites of these fatty acids demonstrates that obesity is correlated to an accelerated systemic 20:4w6 flux (a loop of transport of 20:4w6 from liver to peripheral membranes and return to the liver via LDL/HDL, rather than to impairment in arachidonic acid production per se).

The significance of changes in the fatty acid content of the diet over time is unclear. Some researchers have recommended restriction in the diet of food containing unusual isomeric unsaturated fatty acids, and substitution of oils having a high level of omega-3 linoleic acid compared to omega-6 linoleic acid. See, for example, Holman, et al., PNAS, 88: 4830 (1991). Whether the shifts in diet are truly responsible for the rise in obesity will probably not be known until large scale, long term double blinded clinical trials have been conducted.

It is clear that the phenomenon of obesity is an exceedingly complex biochemical condition. From a physiological standpoint, obesity is no less complex. The utilization of food energy involves three pathways. The basal or resting metabolic rate is the rate at which energy is expended simply to maintain the body intact, and constitutes approximately 70 percent of energy utilization in the average sedentary individual. Another 10 percent of energy is heat generated by the digestion and processing of food. Finally, about 20 percent of food energy is consumed during physical activity.

The allocation of these energy utilizations has some very interesting effects. For example, when an obese individual is subjected to food restriction, the body's reaction is to dramatically reduce basal metabolism. Thus, the weight loss from diet restriction is always less than the loss predicted from the caloric deficit, resulting in substantial deviation from the Kleiber curve. (For a detailed discussion of energy management and the evidence of physiological regulation, see Stunkard and Wadden, eds., *Obesity: Theory and Therapy*, 2nd ed., Raven Press: 1993). As the body gains weight, both the number of adipocytes and their lipid content increases. During food restriction, basal metabolism declines, and the lipid content, but not cell numbers of adipocytes decrease. When caloric load is resumed, most of the food energy is directed into lipogenesis (to restore the obese weight set point), and there is a great excess of lipid depleted lipocytes available to absorb the new lipids. This explains why dieters tend to gain weight rapidly after discontinuing a fat-restricted diet.

Apart from diet, several methods of chemically treating obesity with pharmacologically active substances have been identified. However, these methods involve certain risk. Caffeine and amphetamine based diet aids may be addictive and adversely affect other areas of health. The combination of fenfluramine and phentermine has been proven to cause heart valve disease. Other dietary aids are available over the counter. Almost all of these chemical remedies have as their objective, weight loss through reduced food intake, brought about by appetite suppression. The ideal treatment for obesity would achieve weight reduction through a safe intervention—the natural biochemical and physiological processes which direct food into tissue mass.

SUMMARY OF THE INVENTION

One of the great challenges in modern medicine is to devise a safe and effective method of treating obesity and/or achieving healthy reductions in body weight to a predetermined level ideal for the individual. Under current approaches the cure is often worse than the disease itself, as in the case of health or even life threatening side effects. It is therefore an object of the present invention to provide a safe method of reducing weight and treating obesity. A second serious problem with obesity is that even when excess weight is lost, the effect is only temporary, and the individual regains weight soon after abandoning a diet or other treatment method. Heretofore, only lifelong adherence to a carefully formulated diet, and a program of regular exercise have succeeded in sustaining long term results. Accordingly, it is a second object of the invention to provide a lasting remedy for obesity without unpleasant restrictions in diet, or difficult to maintain exercise programs.

In the present method, conjugated linoleic acid is orally administered in a therapeutically effective amount to humans with clinical obesity or a nutritionally effective amount to humans of normal weight, to cause a loss of the desired weight, and then continuously administered in a maintenance dose to prevent regaining the lost weight. For the individual, this may be a daily dosage of between 0.1 and 15 grams, preferably about 2 grams. The initial dose may be greater (up to 15 grams per day)for the grossly obese individual, although the rate of metabolism may affect the actual working dose. An advantage of CLA is that, unlike restrictive diets, its administration does not compromise healthy nutrition, and does not require the individual to forego favorite foods.

The CLA may be a mixture of the eight possible isomers cis-9, trans-11; cis-9, cis-11; trans-9, cis-11; trans-9, trans-11; cis-10, cis-12; cis-10, trans-12; trans-10, cis-12, and trans-10, trans-12 octadecadienoic acids. Since certain of these are thought to possess more biological activity than others, the mixture may be a more purified mixture consisting of predominantly the cis-9, trans-11 and trans-10, cis-12 isomers, or simply the cis-9, trans-11 isomer alone.

In a typical regimen, an individual will begin the weight loss program by ingesting up to several grams of CLA with each meal, and monitoring body weight over a two week period. The CLA may be provided in the form of a pill or as a component of a prepared food product. In the event that no weight is lost, the dose is increased and the trial repeated. Once the desired weight has been attained, a proper maintenance level can be found by gradually reducing the dose and continuing to monitor weight to assure there is no gain.

DETAILED DESCRIPTION OF THE PREFERRED EMBODIMENTS

Conjugated linoleic acid (CLA, also known as octadecadienoic acid), has been identified in meat and dairy products by Chin et al., *J. Food Comp. Anal.* 5: 185–197 (1992). CLA is a collective term for positional and geometric isomers of linoleic acid with conjugated double bonds at carbon atoms 10 and 12 or 9 and 11 in the various cis-trans conformations. CLA differs from ordinary linoleic acid which has double bonds at carbon atoms 9 and 12.

CLA has several unique properties when used as a food additive. U.S. Pat. No. 5,554,646 discloses the use of CLA to reduce the percentage of fat in relation to total body mass. U.S. Pat. No. 5,428,072 discloses the use of CLA for increasing the efficiency of feed conversion in animals, which results in more non-fat tissue being formed in relation to weight gain. U.S. Pat. Nos. 5,430,066 and 5,585,400 disclose the use of CLA to prevent weight loss due to immune stimulation and to treat immune hypersensitivity. The foregoing patents are incorporated herein by reference. CLA also has anticarcinogenic activity, as shown in Belury, Nut. Rev. 53 (4): 83–9 (1995). Therefore, CLA may be used for increasing or maintaining weight gain in animals. CLA has not been shown heretofore to have any effect on weight reduction, particularly in obese humans.

The mechanism by which CLA mediates these effects is not known, although some biochemical models involving fat partitioning and shifts in fatty acid precursor mediated synthesis of end product prostaglandins and leukotrienes have been proposed. It is known that CLA is taken up in triglycerides and phospholipids, and deposited in fat stores. The precise structure and distribution of these lipids is not known. Nor is it known whether there is a competitive incorporation amongst two or more isomers, or a preferential deposition of certain isomers in some lipid species over others.

CLA is a mixture of one or all of the isomers of octadecadienoic acid including the cis-9, trans-11; cis-9, cis-11; trans-9, cis-11; trans-9, trans-11; cis-10-cis -12; cis-10, trans-12; trans-10, cis-12; and trans-10, trans-12 isomers. The cis-9,trans-11 and trans-10, cis-12 isomers are thought to have the most biological activity. Therefore, these isomers may be used in a purified form.

In the preferred embodiment of the present invention, a safe and effective nutritional or therapeutic amount of CLA is orally administered to a human to decrease body weight. CLA may be administered to obese and non-obese humans. Because CLA is a non-toxic, naturally occurring food ingredient and not a drug, CLA may be consumed as a part of a normal diet and finds use as a part of everyday nutrition in people without obesity. A nutritionally effective amount is that amount CLA that, when ingested in purified form or as food supplement results in a reduction in body weight without impairing or interfering with proper nutrition. Accordingly, administration of a nutritionally effective amount of CLA achieves weight loss without sensory deprivation associated with reduction in food intake. CLA may also be used to treat humans with slight to profound clinical obesity. When treating humans with clinical obesity, a therapeutically effective amount of CLA is administered. A therapeutically effective amount is that amount which causes a reduction in weight of a clinically obese person. In the present invention, about 0.1 to 15 grams of CLA may be administered per day, preferably about 1 to 5 grams per day may be administered and most preferably about 1.8 grams per day may be administered. In general, the amount of CLA administered is not critical as long as it is enough to be nutritionally or therapeutically effective. The amounts of CLA deemed nutritionally or therapeutically effective are those which result in measurable weight loss when administered over a two week period or longer.

It is anticipated that there will be some variation in effectiveness because of differences among individuals in parameters such as body weight, basal metabolism, exercise, and other aspects of the diet. The individual should begin with the preferred 1.8 gram dose for an initial two week period, and then, if no weight loss is experienced, gradually increase the CLA dose up to about 10–15 grams per day.

Derivatives of CLA may also be utilized in the present invention. The CLA may be free or bound through ester linkages. For example, the CLA may be provided in the form of an oil containing CLA triglycerides. The triglycerides may be partially or wholly comprised of CLA attached to a glycerol backbone. Furthermore, the CLA may be in the form of a non-toxic salt, such as a potassium or sodium salt, which is formed by reacting chemically equivalent amounts of the free acids with an alkali hydroxide at a pH of about 8 to 9. The CLA may also be used in liquid, gel or powdered forms.

The preferred method of administration is oral. The CLA may be formulated with suitable carriers such as starch, sucrose or lactose in tablets, capsules, solutions and emulsions. The tablet or capsule of the present invention may be coated with an enteric coating which dissolves at a pH of about 6.0 to 7.0. A suitable enteric coating which dissolves in the small intestine but not in the stomach is cellulose acetate phthalate.

A nutritionally effective amount of CLA may also be provided as a supplement in various prepared food products. For the purposes of this application, prepared food product means any natural, processed, diet or non-diet food product to which CLA has been added. The CLA may be added in the form of free fatty acids or as an oil containing partial or whole triglycerides of CLA. Therefore, CLA may be directly incorporated into many prepared diet food products, including, but not limited to diet drinks, diet bars and prepared frozen meals. Furthermore, CLA may be incorporated into many prepared non-diet products, including, but not limited to candy, snack products such as chips, prepared meat products, milk, cheese, yogurt and any other fat or oil containing foods.

CLA is also susceptible to oxidation. Therefore it is desirable to package CLA for human use with suitable antioxidants such as lecithin, tocopherols, ascorbate, ascorbyl palmitate or spice extracts such as rosemary extract.

Currently, most CLA is manufactured by the alkali isomerization process. Preferably, an oil containing a high amount of linoleic acid such as sunflower oil, evening primrose oil or safflower oil is reacted in an inert nitrogen environment with potassium hydroxide and a solvent such as ethylene glycol at about 180° C. for about 2.5 hours. The reaction product is acidified and extracted with hexane, and the hexane removed by vacuum. For a complete description of the production of CLA by alkali isomerization, see U.S. Pat. No. 5,554,646, incorporated herein by reference. Most preferably, the CLA may be produced by the continuous flow alkali isomerization process described in U.S. Pat. No. 4,164,505, incorporated herein by reference. The reaction product obtained from these processes is a mixture of CLA, linoleic acid and the other fatty acids found in the source oil. Generally, the amount of CLA derived from alkali isomerization of sunflower oil is about 60%. of the total free fatty acid product.

Another method of producing a preparation consisting of primarily cis-9, trans-11 CLA is disclosed in U.S. Pat. No. 5,674,901, incorporated herein by reference. In that method, linoleic acid containing oil is incubated with the microorganism *Butyrivibrio fibrisolvens*. *B. fibrisolvens* contains an $\Delta^{12}$-cis,$\Delta^{11}$-isomerase which converts linoleic acid into cis-9, trans-11 CLA.

Dietary supplementation with CLA results in weight loss in human patients. This is in contrast to studies disclosed in U.S. Pat. Nos. 5,428,072, 5,554,646 and 5,430,066 which disclose the dietary use of CLA to increase feed efficiency, increase weight gain, and maintain weight in the face of environmental challenges. From those studies, it could be predicted that dietary supplementation with CLA would increase the efficiency of food use resulting in weight gain or at least the maintenance of weight at a fixed level while body fat decreased. Furthermore, the literature suggests that increasing the amount of omega-6 fatty acid, fatty acids with trans configurations and unusual isomers of polyunsaturated fatty acids in the diet is undesirable and may lead to obesity. CLA is an unusual omega-6 polyunsaturated fatty acid with trans isomers. Dietary supplementation with CLA presents an effective treatment for weight reduction which may be used alone or in combination with other treatment regimes.

EXAMPLE

The efficacy of the oral administration of CLA for reducing weight in humans was determined. The study was carried out as a randomized placebo controlled double-blind study in 20 healthy volunteers, who after having received information about the aim of the study, gave their consent to participate.

The duration of the study was 3 months and the following parameters were registered initially and every 4 weeks: Body Weight (BW), Body Fat % (BF). Height was registered initially and tolerability was asked for at each control.

The investigation preparations (Tonalin CLA and placebo) were given in form of capsules. The capsules used were identical in appearance and were packed in the same way (blister packs).

The study medications were randomized, so that half of the subject received Tonalin CLA capsules and the other half placebo. The dose was six 500 mg capsules per day with dosage scheme of 2 capsules in the morning, 2 at lunch time and 2 at dinner. The participants were asked to take the capsules together with food and to swallow the capsules together with 200 ml of water on each occasion. Each Tonalin capsule contained 0.3 g of pure CLA.

The subjects were asked not to carry out any changes in their diet and lifestyle while participating in the study. The body composition measurements were carried out using near infrared (NIR) technology and the instrument used was a Futrex 5000A (Futrex, Inc., Gaithersburg Md.; USA). All measurements were done in triplicate and the average values were used for statistical comparison. The biceps on the best arm was used as a measuring site.

Compliance to the dose scheme was checked by counting returned capsules. 80% of the recommended dose was the lowest level accepted.

20 subjects were included in the study and 18 concluded the study according to the protocol. 2 subjects withdrew from the study due to tolerability problems (see Tolerability). In Table 1, the anthropometric data for the subjects is listed and the data shows that the two groups are comparable with respect to these parameters when entering the study.

TABLE 1

ANTHROPOMETRIC DATA FOR THE TWO STUDY GROUPS

| GROUP | N | GENDER | AGE | WEIGHT * | HEIGHT * | BF % | BMI |
|---|---|---|---|---|---|---|---|
| CLA | 10 | 5F/5M | 27.5 | 156.6 lbs. | 175.0 | 21.3 | 23.2 |
| PLACEBO | 10 | 5F/5M | 28.0 | 158.9 lbs. | 176.0 | 22.0 | 23.3 |

The units are as follows: Age (years); Weight (lbs.); Height (cm): BF (%.) and BMI (Body Mass Index) (kg/m2).

The study groups consisted of both genders and all had a normal body weight which is reflected by the BMI values which, on an average, are well below 25. In Table 2, the development in the parameters registered on a monthly basis are shown in the two groups at the end of the study as compared to the initial values.

TABLE 2

BODY WEIGHT AND BODY FAT AT THE START AND END OF THE STUDY

| GROUP | N | INITIAL BW* | BW AFTER 3 MO.* | INITIAL BF % | BF% AFTER 3 MO. |
|---|---|---|---|---|---|
| CLA | 10 | 156 lbs. | 154.5 lbs. | 21.3 | 17.0 |
| PLACEBO | 10 | 158 lbs. | 159.4 lbs. | 22.0 | 22.4 |

As can be seen from the data presented in Table 2 the participants are weight s table during the study period. There is a drop in W in the group receiving Tonalin (CLA). Turning to the BF measurements, there is a reduction in BF in the CLA group (a drop in BF from 21.3% to 17.0% (p<0.05)), while no change is seen in the placebo group.

Two subjects decided to stop intake of the capsules in the study period because they experienced unpleasant gastrointestinal upsets. One subject stopped intake after 4 weeks (Tonalin CLA) and the other one after 8 weeks (placebo).

What is claimed is:

1. A method of reducing weight in humans, said method comprising orally administering a nutritionally effective amount of conjugated linoleic acid.

2. A method for treating obesity in humans, said method comprising orally administering a therapeutically effective amount of conjugated linoleic acid, said therapeutic amount sufficient to reduce bodyweight.

3. The methods of claims 1 or 2, wherein said nutritionally effective and said therapeutically effective amounts of conjugated linoleic acid are about 0.1 to 15 grams per day.

4. The methods of claims 1 or 2 wherein said conjugated linoleic acid is a mixture of octadecadienoic acid isomers selected from the group of cis-9, trans-11; cis-9, cis-11; trans-9, cis-11; trans-9, trans-11; cis-10, cis-12; cis-10, trans-12, trans-10, cis-12; and trans-10, trans-12 octadecadienoic acid.

5. The methods of claims 1 or 2 wherein said nutritionally and therapeutically effective amounts of conjugated linoleic acid are provided in a prepared food product.

6. The methods of claims 1 or 2 wherein the conjugated linoleic acid is cis-9, trans-11 octadecadienoic acid.

7. A method of reducing weight in humans, said method comprising orally administering about 1 to 5 grams per day of a mixture of octadecadienoic acids selected from the group consisting of cis-9, trans-11; cis-9, cis-11; trans-9, cis-11; trans-9, trans-11; cis-10, cis-12; cis-10, trans-12; trans-10, cis-12; and trans-10, trans-12 octadecadienoic acids.

8. A method of treating obesity in humans, said method comprising orally administering about 1 to 5 grams per day of a mixture of octadecadienoic acids selected from the group consisting of cis-9, trans-11; cis-9, cis-11; trans-9, cis-11; trans-9, trans-11; cis-10, cis-12; cis-10, trans-12; trans-10, cis-12; and trans-10, trans-12 octadecadienoic acids, so that bodyweight is reduced.

* * * * *